(12) United States Patent
Parthasaradhi Reddy et al.

(10) Patent No.: US 7,750,153 B2
(45) Date of Patent: Jul. 6, 2010

(54) PROCESS FOR THE PREPARATION OF DIDANOSINE USING NOVEL INTERMEDIATES

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 580 days.

(21) Appl. No.: 11/570,358

(22) PCT Filed: Jul. 5, 2005

(86) PCT No.: PCT/IN2005/000229

§ 371 (c)(1),
(2), (4) Date: Dec. 11, 2006

(87) PCT Pub. No.: WO2007/004230

PCT Pub. Date: Jan. 11, 2007

(65) Prior Publication Data

US 2008/0293938 A1 Nov. 27, 2008

(51) Int. Cl.
*C07D 473/30* (2006.01)
*C07H 19/073* (2006.01)

(52) U.S. Cl. .................................. 544/265; 536/27.14
(58) Field of Classification Search .................. None
See application file for complete search history.

(56) References Cited

U.S. PATENT DOCUMENTS

| 5,290,927 | A | | 3/1994 | Honda et al. |
| 5,451,671 | A | | 9/1995 | Shiragami et al. |
| 5,455,339 | A | * | 10/1995 | Chu ........................ 536/27.14 |
| 5,466,793 | A | * | 11/1995 | Honda et al. ............... 536/55.3 |
| 6,207,650 | B1 | | 3/2001 | Bogardus et al. |
| 7,053,192 | B2 | * | 5/2006 | Li et al. ........................ 536/7.4 |
| 2005/0135999 | A1 | * | 6/2005 | Elomari et al. .............. 423/706 |
| 2006/0094870 | A1 | | 5/2006 | Torii et al. ................ 536/27.21 |
| 2006/0251728 | A1 | * | 11/2006 | Himmelsbach et al. ..... 424/489 |
| 2007/0032435 | A1 | * | 2/2007 | Alani et al. .................... 514/18 |
| 2007/0249544 | A1 | * | 10/2007 | Himmelsbach et al. ....... 514/27 |
| 2008/0004448 | A1 | * | 1/2008 | Wayne et al. ............. 546/276.7 |
| 2008/0089835 | A1 | * | 4/2008 | Burton ....................... 423/706 |
| 2008/0103186 | A1 | * | 5/2008 | Glover et al. ................ 514/395 |
| 2008/0319024 | A1 | * | 12/2008 | Greil et al. .................. 514/342 |
| 2009/0176983 | A1 | * | 7/2009 | Dova et al. .................. 544/242 |

FOREIGN PATENT DOCUMENTS

| EP | 0206497 A2 | | 5/1986 |
| EP | 1887013 A1 | * | 2/2008 |
| WO | WO 2007/004230 A2 | | 1/2007 |

* cited by examiner

*Primary Examiner*—Mark L Berch
(74) *Attorney, Agent, or Firm*—Caesar, Rivise, Bernstein, Cohen & Pokotilow, Ltd.

(57) ABSTRACT

The present invention relates to novel crystalline alkali metal and alkaline earth metal salts of 2',3'-dideoxy-2',3'-didehydroinosine. The present invention also provides a novel process for preparation of didanosine in high yield and purity using novel intermediates. Thus, for example, 5'-O-acetyl-2',3'-dideoxy-2',3'-didehydroinosine is reacted with monomethyl amine to give 2',3'-dideoxy-2',3'-didehydro inosine, which is then reacted with sodium hydroxide and crystallized to give crystalline 2',3'-dideoxy-2',3'-didehydroinosine sodium salt. 2',3'-Dideoxy-2',3'-didehydroinosine sodium salt is hydrogenated using raney nickel catalyst in aqueous medium and then neutralized with hydrochloric acid to yield didanosine.

26 Claims, 1 Drawing Sheet

PROCESS FOR THE PREPARATION OF DIDANOSINE USING NOVEL INTERMEDIATES

FIELD OF THE INVENTION

The present invention provides a novel process for the preparation of didanosine in high yield and purity using novel intermediates. The present invention also relates to novel crystalline alkali metal and alkaline earth metal salts of 2',3'-dideoxy-2',3'-didehydroinosine.

BACKGROUND OF THE INVENTION

European Patent No. EP 206497 disclosed certain 2',3'-dideoxynucleosides and pharmaceutically acceptable derivatives thereof. These compounds are antiviral agents. Among them didanosine, chemically 2',3'-dideoxyinosine is a selective HIV-I inhibitor and can be used as medicaments in the treatment and prophylaxis of viral, especially retroviral infections. Didanosine is represented by the following structure:

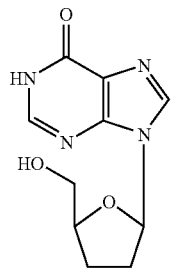

I

U.S. Pat. No. 5,451,671 described purification of crude didanosine by extracting didanosine with a solvent such as an alcohol from a basic solution having a pH of not less than 13 of crude didanosine.

U.S. Pat. No. 5,451,671 also described purification method of didanosine by passing a resin containing column at a pH of not less than 11.

U.S. Pat. No. 6,207,650 disclosed that pure didanosine can be obtained by isolating didanosine as alkali metal or alkaline earth metal salt of didanosine as a crystalline solid and then converting the salt to didanosine.

Even though, the process described (above) in U.S. Pat. No. 6,207,650 yields pure didanosine, the yields obtained by the crystallization as an alkali metal or alkaline earth metal salt of didanosine are very low and so, there remains a need for a process for purification of didanosine that can yield pure didanosine in high purity and in high yield.

U.S. Pat. No. 5,290,927 (column 11, lines 24-29) indicated that water, if contained during the catalytic reduction of 2',3'-didehydro-2',3'-dideoxyinosine to 2',3'-dideoxyinosine greatly accelerates the decomposition of substrate and indicated, so, that the reaction is preferably conducted in an non-aqueous medium.

We have surprisingly found that even though 2',3'-dideoxy-2',3'-didehydroinosine cannot be hydrogenated in aqueous medium, their alkali metal or alkaline earth metal salts can be hydrogenated smoothly and completely to give 2',3'-dideoxyinosine alkali metal or alkaline earth metal salts. The salts thus obtained can be converted to didanosine by known methods.

It has also been found that didanosine or didanosine alkali metal or alkaline earth metal salts, which are obtained by the hydrogenation of alkali metal or alkaline earth metal salts of 2',3'-dideoxy-2',3'-didehydroinosine have very purity and the product is obtained in high yield.

It has also been found that the alkali metal or alkaline earth metal salts of 2',3'-dideoxy-2',3'-didehydroinosine can be isolated from a solution or reaction mass as a crystalline solid. The crystallization of the alkali metal or alkaline earth metal salts of 2',3'-dideoxy-2',3'-didehydroinosine provides a purification method for finally preparing didanosine.

Thus, the crystalline alkali metal or alkaline earth metal salts of 2',3'-dideoxy-2',3'-didehydroinosine provides valuable intermediate for the preparation of didanosine or an alkali metal or alkaline earth metal salt of didanosine.

U.S. Pat. No. 6,207,650, which is incorporated herein by reference, discloses crystalline alkali metal or alkaline earth metal salts of didanosine and their use in pharmaceutical formulations and their use as an intermediate for preparing didanosine.

The present invention also provides a process for preparing sodium salt of didanosine using novel intermediates.

One object of the present invention is to provide a novel process for preparing didanosine in high yield and purity using novel intermediates.

Another object of the present invention is to provide novel crystalline alkali metal and alkaline earth metal salts of 2',3'-dideoxy-2',3'-didehydroinosine and processes for preparing them.

DETAILED DESCRIPTION OF THE INVENTION

According to one aspect of the present invention, there is provided a novel crystalline alkali metal or alkaline earth metal salt of 2',3'-dideoxy-2',3'-didehydroinosine of formula II:

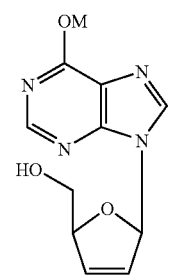

II wherein M is an alkali metal ion such as $Na^+$, $K^+$ or $Li^+$; or an alkaline earth metal ion such as $Ca^{2+}$ or $Mg^{2+}$.

According to another aspect of the present invention, a process is provided for preparation of crystalline alkali metal or alkaline earth metal salt of 2',3'-dideoxy-2',3'-didehydroinosine, which comprises crystallizing the alkali metal or alkaline earth metal salt of 2',3'-dideoxy-2',3'-didehydroinosine from a solution of alkali metal or alkaline earth metal salt of 2',3'-dideoxy-2',3'-didehydroinosine in a solvent selected from alcoholic solvents such as methanol, ethanol, isopropyl alcohol, tert-butyl alcohol and n-butyl alcohol, water, ethyl acetate, acetonitrile, and a mixture thereof.

A preferable solvent is selected from the group consisting of methanol, ethanol, water and a mixture thereof.

A preferable alkali metal ion is $Na^+$ or $K^+$ and a more preferable alkali metal ion is $Na^+$. A preferable alkaline earth metal ion is $Mg^{2+}$.

Preferably, the invention particularly relates to a novel crystalline 2',3'-dideoxy-2',3'-didehydroinosine sodium salt of the formula IIa:

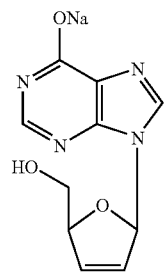

IIa

Crystalline 2',3'-Dideoxy-2',3'-didehydroinosine sodium salt is characterized by an x-ray powder diffraction spectrum having peaks expressed as 2θ at about 15.6, 17.3, 18.0, 21.5, 23.4, 24.7, 27.2 and 29.8 degrees. FIG. 1 shows a typical X-ray powder diffraction spectrum of crystalline 2',3'-dideoxy-2',3'-didehydroinosine sodium salt of the present invention.

According to another aspect of the present invention, there is provided a novel process for preparing didanosine of the formula I.

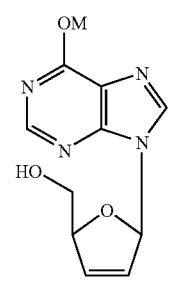

I which comprises:
a) hydrogenating an aqueous solution of an alkali metal or alkaline earth metal salt of 2',3'-dideoxy-2',3'-didehydroinosine of the formula II:

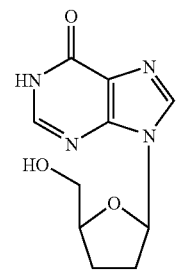

II wherein M is an alkali metal ion such as $Na^+$, $K^+$ or $Li^+$; or an alkaline earth metal ion such as $Ca^{2+}$ or $Mg^{2+}$;
by using an hydrogenating metal catalyst; and
b) neutralizing with an acid to obtain didanosine of the formula I.

Any of the conventionally used hydrogenating metal catalysts may be used. Preferably, hydrogenation may be carried out by using raney nickel, palladium, platinum, rhodium. These catalysts may be used as their metal form or in the form of their compounds such as oxides. The catalyst used may be supported on an inert support. Some examples of the catalysts that may be used are raney nickel, palladium, platinum, palladium carbonate, platinum oxide, palladium on carbon, palladium on alumina and palladium on $CaCO_3$.

The hydrogenation reaction is preferably carried out at a pressure below about 5 $Kg/cm^2$, more preferably at below about 3 $Kg/cm^2$ and still more preferably at about 1-2 $kg/cm^2$.

Preferably the hydrogenation reaction is carried out at about 5-50° C., more preferably at about 10-30° C. and still more preferably at about 10-20° C.

The hydrogenation may also be carried out in the presence of water plus any other solvent. The solvent, which can be used along with water, may be selected from alcohols such as methanol, ethanol, isopropyl alcohol, tert-butyl alcohol, n-butyl alcohol and a mixture thereof.

The choice of the acid in step-(b) is not critical and any inorganic or organic acid may be used. Examples of inorganic acids are hydrochloric acid, sulfuric acid and phosphoric acid. Examples of organic acids are carboxylic acids such as formic acid and acetic acid; sulfonic acids such as methanesulfonic acid and toluenesulfonic acid.

The didanosine obtained above may be worked up by conventional means or by a known method to obtain didanosine as a solid.

Figure 1:
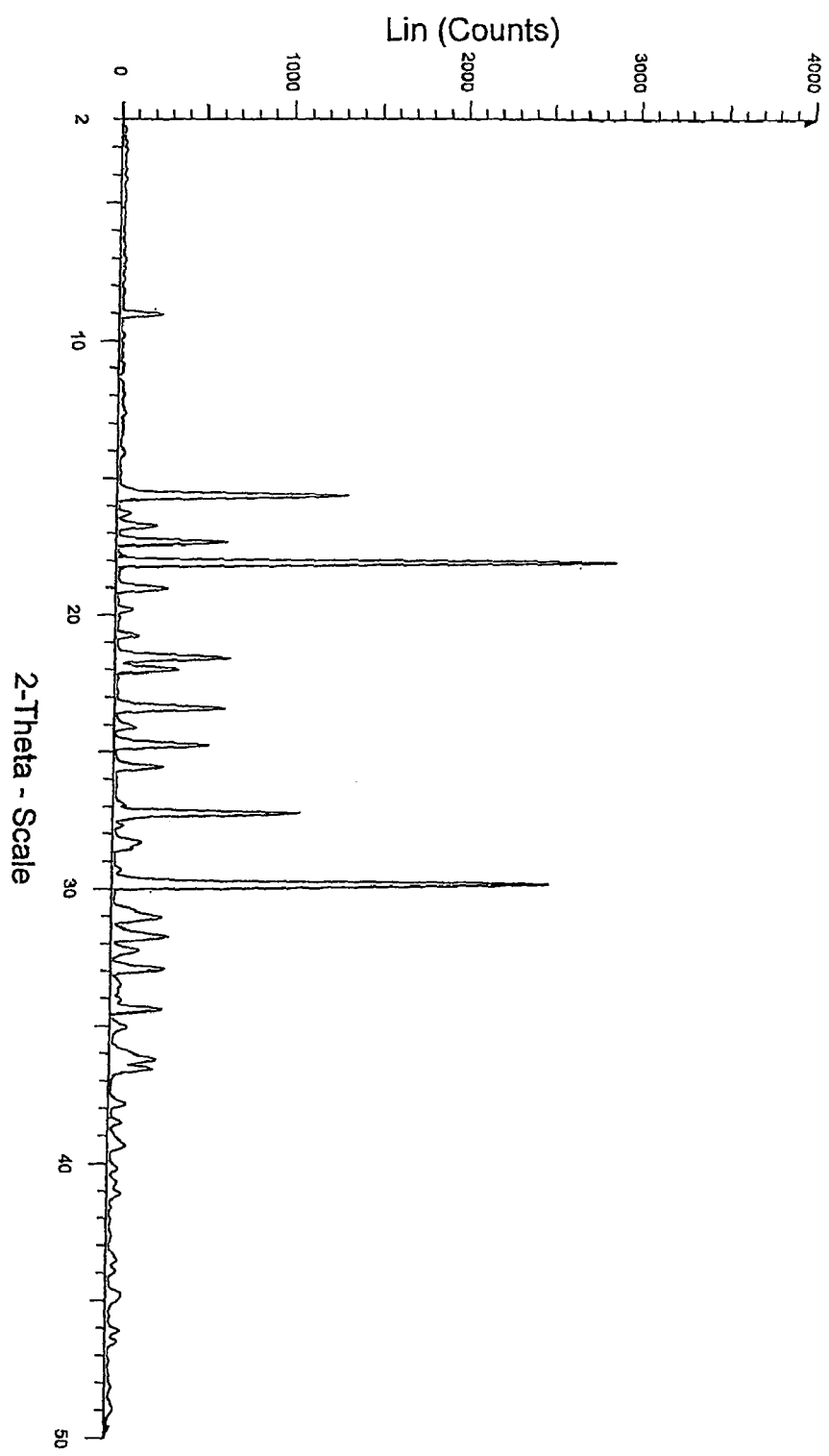
FIG. 1 shows typical X-ray powder diffraction spectrum of the crystalline 2',3'-dideoxy-2',3'-didehydroinosine sodium salt of the present invention.

X-Ray powder diffraction spectrum was measured on a Bruker axs D8 advance x-ray powder diffractometer having a Copper-Kα radiation. Approximately 1 gm of sample was gently flattened on a sample holder and scanned from 2 to 50 degrees two-theta, at 0.03 degrees two-theta per step and a step time of 0.5 seconds. The sample was simply placed on the sample holder. The sample was rotated at 30 rpm at a voltage 40 KV and current 35 mA.

The invention will now be further described by the following examples, which are illustrative rather than limiting.

EXAMPLE 1

5'-O-Acetyl-2',3'-dideoxy-2',3'-didehydroinosine (100 gm) is added to 25% monomethyl amine (360 ml) at 25-35° C. and stirred for 4-5 hours at 25-35° C. The mass is filtered on a celite bed, washed with methanol (50 ml) and the solvent is distilled off completely under reduced pressure at below 70° C. Methanol (25 ml) is added to the filtrate, the solvent is distilled off completely, and methanol (25 ml) is again added and co-distilled. To the mass, acetone (25 ml) is added, co-distilled, again co-distilled with 25 ml of acetone at below 70° C. and acetone (400 ml) is added. The contents are cooled to 25-35° C., stirred for 2 hours to 2 hours 30 minutes at 25-35° C. Then the reaction mass is cooled to 0-10° C. and stirred for 1 hour to 1 hour 30 minutes. material is filtered, washed with acetone (80 ml) and dried at 55-65° C. to give 62.5 gm of 2',3'-dideoxy-2',3'-didehydroinosine (HPLC Purity: 98.14%).

EXAMPLE 2

2',3'-Dideoxy-2',3'-didehydroinosine (55 gm) is added to ethanol (330 ml) and then sodium hydroxide flakes (7 gm) are added during 30 minutes to 1 hour at below 50° C. To the contents 40% sodium hydroxide solution (35 ml) is added at below 50° C. and stirred for 30 minutes at 40-50° C. Water (165 ml) is added to the reaction mass and stirred for 11-12 hours at 25-30° C. The reaction mass is cooled to 5-15° C. and stirred for 1 hour. The solid is filtered, washed with ethanol (45 ml) and dried at 50-55° C. to give 57.2 gm of 2',3'-dideoxy-2',3'-didehydroinosine sodium salt (HPLC Purity: 99.63%).

EXAMPLE 3

2',3'-Dideoxy-2',3'-didehydroinosine sodium salt (50 gm) is added to water (180 ml) and stirred for 20 minutes at 25-35° C. Then the contents are hydrogenated under nitrogen atmosphere at 1.5-2.0 kg/cm² hydrogen pressure at 15-20° C. using raney nickel catalyst for 7-8 hours. The reaction mass is filtered on a celite bed and washed with water (25 ml). To the filtrate activated carbon (2 gm) is added and stirred for 20 minutes. The mass is filtered on a celite bed and washed with water (25 ml). The filtrate is cooled to 5-15° C., the pH is adjusted to 7.0-8.0 with dilute hydrochloric acid (13 ml water+13 ml conc. HCl) at 5-15° C. and stirred for 2 hours 30 minutes. Filtered the mass, washed with water (40 ml). The resulting wet cake is added to water (120 ml), the temperature is raised to 65-75° C. and stirred for 20 minutes at the same temperature. The resulting solution is cooled to 25-35° C. and stirred for 1 hour 30 minutes. The reaction mass is then cooled to 10-15° C. and stirred for 1 hour 30 minutes. Filtered the solid, washed with the 40 ml of water and dried at 55-60° C. to give 30.5 gm of didanosine (HPLC Purity: 99.85%).

Without further elaboration of the foregoing will so fully illustrate our invention that others may, by applying current or future knowledge, adapt the same for use under various conditions of service.

We claim:
1. A crystalline alkali metal or alkaline earth metal salt of 2',3'-dideoxy-2',3'-didehydroinosine of the formula II:

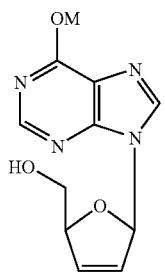

wherein M is an alkali metal ion selected from the group consisting of Na⁺, K⁺ and Li⁺; or an alkaline earth metal ion selected from the group consisting of Ca²⁺ and Mg²⁺.

2. A process for the preparation of the crystalline alkali metal or alkaline earth metal salt of 2',3'-dideoxy-2',3'-didehydroinosine of claim 1, which comprises crystallizing the alkali metal or alkaline earth metal salt of 2',3'-dideoxy-2',3'-didehydroinosine from a solution of alkali metal or alkaline earth metal salt of 2',3'-dideoxy-2',3'-didehydroinosine in a solvent.

3. The process as claimed in claim 2, wherein the solvent is an alcoholic solvent selected from the group consisting of methanol, ethanol, isopropyl alcohol, tert-butyl alcohol, n-butyl alcohol, water, ethyl acetate, acetonitrile, and mixtures thereof.

4. The process as claimed in claim 3, wherein the solvent is selected from methanol, ethanol, water and mixtures thereof.

5. The process as claimed in claim 1 wherein the alkali metal ion is Na⁺ or K⁺.

6. The process as claimed in claim 5 wherein the alkali metal ion is Na⁺.

7. The process as claimed in claim 1 wherein the alkaline earth metal ion is Mg²⁺.

8. A crystalline 2',3'-dideoxy-2',3'-didehydroinosine sodium salt of the formula IIa:

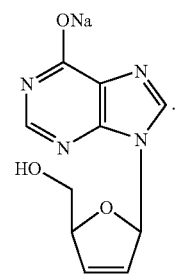

9. Crystalline 2',3'-dideoxy-2',3'-didehydroinosine sodium salt as claimed in claim 8, characterized by an x-ray powder diffraction spectrum measured using Cu—Kα radiation having peaks expressed as 2θ at 15.6, 17.3, 18.0, 21.5, 23.4, 24.7, 27.2 and 29.8 degrees.

10. A process for the preparation of didanosine of the formula I:

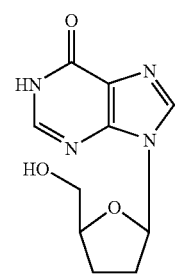

which comprises:
a) hydrogenating an aqueous solution of an alkali metal or alkaline earth metal salt of 2',3'-dideoxy-2',3'-didehydroinosine of the formula II:

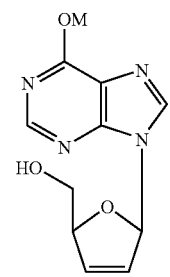

wherein M is an alkali metal ion selected from the group consisting of $Na^+$, $K^+$ and $Li^+$;

or an alkaline earth metal ion selected from the group consisting of $Ca^{2+}$ and $Mg^{2+}$;

by using an hydrogenating metal catalyst; and b) neutralizing with an acid to obtain didanosine of the formula I.

11. The process as claimed in claim 10, wherein the hydrogenation metal catalysts are used in their metal form or in the form of their compounds.

12. The process as claimed in claim 10, wherein the hydrogenation metal catalyst used is supported on an inert support.

13. The process as claimed in claim 10, wherein the hydrogenation metal catalyst is selected from raney nickel, palladium, platinum, rhodium, palladium carbonate, platinum oxide, palladium on carbon, palladium on alumina and palladium on $CaCO_3$.

14. The process as claimed in claim 13 wherein the hydrogenation metal catalyst is raney nickel.

15. The process as claimed in claim 10 wherein the hydrogenation reaction is carried out at the pressure below about 5 $Kg/cm^2$.

16. The process as claimed in claim 15 wherein the hydrogenation reaction is carried out at the pressure below about 3 $Kg/cm^2$.

17. The process as claimed in claim 16 wherein the hydrogenation reaction is carried out at the pressure about 1-2 $Kg/cm^2$.

18. The process as claimed in claim 10 wherein the hydrogenation reaction is carried out at about 5-50° C.

19. The process as claimed in claim 18 wherein the hydrogenation reaction is carried out at about 10-30° C.

20. The process as claimed in claim 19 wherein the hydrogenation reaction is carried out at about 10-20° C.

21. The process as claimed in claim 10 wherein the hydrogenation reaction is carried out in the presence of water plus any other solvent.

22. The process as claimed in claim 21 wherein the solvent is an alcohol selected from the group consisting of methanol, ethanol, isopropyl alcohol, tert-butyl alcohol, n-butyl alcohol, and mixtures thereof.

23. The process as claimed in claim 10 wherein the acid is an inorganic acid.

24. The process as claimed in claim 23 wherein the inorganic acid is selected from hydrochloric acid, sulfuric acid, phosphoric acid.

25. The process as claimed in claim 23 wherein the organic acid is a carboxylic acid selected from the group consisting of formic acid, acetic acid, and mixtures thereof, or a sulfonic acid selected from the group consisting of methanesulfonic acid, toluenesulfonic acid, and mixtures thereof.

26. The process as claimed in claim 10 wherein the acid is an organic acid.

* * * * *